(12) United States Patent
Cherif Cheikh et al.

(10) Patent No.: US 7,713,244 B1
(45) Date of Patent: May 11, 2010

(54) SYRINGES FOR ADMINISTERING PASTY OR SEMI-SOLID FORMULATIONS

(75) Inventors: Roland Cherif Cheikh, Issy les Moulineaux (FR); Christophe Aubert, Barcelone (ES)

(73) Assignee: Societe de Conseils de Recherches et d'Applications Scientifiques SCRAS, Paris (FR)

( * ) Notice: Subject to any disclaimer, the term of this patent is extended or adjusted under 35 U.S.C. 154(b) by 0 days.

(21) Appl. No.: 09/787,508

(22) PCT Filed: Sep. 17, 1999

(86) PCT No.: PCT/FR99/02218

§ 371 (c)(1),
(2), (4) Date: May 10, 2001

(87) PCT Pub. No.: WO00/16829

PCT Pub. Date: Mar. 30, 2000

(30) Foreign Application Priority Data

Sep. 18, 1998 (FR) .................................... 98 11699

(51) Int. Cl.
*A61M 5/00* (2006.01)
*A61M 5/315* (2006.01)

(52) U.S. Cl. ...................... 604/218; 604/187
(58) Field of Classification Search ................ 604/195, 604/82, 60, 206, 63, 159, 91, 110, 191, 187, 604/218, 232, 233, 234, 235, 119, 198, 181
See application file for complete search history.

(56) References Cited

U.S. PATENT DOCUMENTS

| | | | | |
|---|---|---|---|---|
| 368,627 A | * | 8/1887 | Threlfall | ..................... 604/183 |
| 2,537,550 A | * | 1/1951 | Roos | ......................... 604/232 |
| 3,110,309 A | * | 11/1963 | Higgins | ...................... 604/201 |
| 3,921,864 A | | 11/1975 | Dawes | |
| 4,008,718 A | * | 2/1977 | Pitesky | ...................... 604/190 |
| 4,024,865 A | | 5/1977 | Howlett | |
| 4,165,646 A | * | 8/1979 | Shapiro | ................... 73/864.13 |
| 4,758,234 A | | 7/1988 | Orentreich et al. | |
| 4,921,486 A | * | 5/1990 | DeChellis et al. | ........... 604/110 |
| 5,290,254 A | | 3/1994 | Vaillancourt | |
| 5,704,918 A | * | 1/1998 | Higashikawa | ............... 604/191 |
| 5,725,508 A | * | 3/1998 | Chanoch et al. | ............ 604/207 |
| 6,475,193 B1 | * | 11/2002 | Park | ......................... 604/191 |

FOREIGN PATENT DOCUMENTS

| | | |
|---|---|---|
| EP | 0 397 977 | 11/1990 |
| EP | 0 824 932 | 2/1998 |
| EP | 0 845 275 | 6/1998 |
| JP | SHO 55-73352 | * 3/1980 |
| JP | 55 073352 | 6/1980 |
| WO | WO 94/07554 | 4/1994 |

* cited by examiner

*Primary Examiner*—Matthew F Desanto
(74) *Attorney, Agent, or Firm*—Young & Thompson (57) ABSTRACT

A syringe for parenteral injection of a semi-solid formulation. The syringe includes a hollow element forming a reservoir for the semi-solid product to be injected between a plunger and a needle hub urged in contact with the reservoir end. The plunger comes into direct contact with the hub when the dose contained in the reservoir-forming element has been injected. The element forming a reservoir and the needle are maintained mutually interlocked at the hub through a mount or case receiving the element forming a reservoir.

43 Claims, 9 Drawing Sheets

SYRINGES FOR ADMINISTERING PASTY OR SEMI-SOLID FORMULATIONS

BACKGROUND OF THE INVENTION

The present invention relates to the parenteral administration, by injection, of medicamental or other formulations which are neither liquids, like the conventional injectable formulations, nor solids, like implants, but are pasty or very viscous and are referred to below as semi-solid formulations.

There are many alternative forms of syringes for the parenteral injection of liquids by means of a needle for parenteral injection. These syringes are practically unusable for the parenteral administration of semi-solid formulations.

Various devices for the parenteral administration of solid formulations, such as implants, are also known, these using trocars of relatively large diameter and being combined with expulsion means allowing the formulation to be expelled from the trocar, for example by withdrawing the latter. Other administration means use catheters.

Also known are syringes intended for the administration of pasty products in dentistry, which allow cements or other materials to be deposited in dental cavities. Examples of such syringes are described in U.S. Pat. Nos. 4,121,587 and 5,603,701 which provide a syringe body in which a piston moves in order to expel the pasty mass through a needle, using means for moving the piston which are based on a threaded rod passing through a complementary immobile thread, in order to gear down the force necessary to expel the pasty mass. However, these syringes are not capable of suitable parenteral injection and are very complex, whether they be specially designed in all their parts or have elements designed to be used with conventional syringe bodies, which means that they are ill-suited to multiple use and are especially in the form of a disposable or non-reusable syringe or carpule.

SUMMARY OF THE INVENTION

One objective of the present invention is to remedy these drawbacks and to provide syringes allowing manual or automatic injection of a semi-solid or pasty formulation, preferably with a generally small volume, 1 ml and especially less than 1 ml or 0.5 ml and down to a few microliters.

Another objective of the invention is to facilitate the administration of semi-solid galenic formulations, including controlled-release formulations, such as those described especially in U.S. Pat. No. 5,595,760.

Another objective of the invention is to produce syringes allowing the injection of such formulations using the conventional methods, for example subcutaneous, intradermic or intramuscular injection, with great accuracy both in the dose actually delivered and in the position of the deposition site.

Another objective of the invention is to allow semi-solid formulations to be delivered, by the syringe, thanks to means of assistance or of force reduction.

Another objective of the invention is to produce these syringes in an extremely simple form, allowing mass production at a very low cost.

Another objective of the invention is to allow extremely easy preloading of the semi-solid formulation to be administered.

Another objective of the invention is to produce syringe assemblies which allow the parenteral administration of different or variable formulation volumes by minimizing the need to produce elements specific to each formulation by volume.

Yet another objective of the invention is to produce syringes using well-known ordinary materials generally used for the parenteral administration of medicaments, such as glass, metal or plastics such as polyethylene or polypropylene, while still withstanding the large forces which have to be deployed for ejecting the pasty formulation through a small-diameter needle.

Another objective of the invention is to produce syringes for the administration of semi-solid products, allowing the operator to check that the end of the needle has not penetrated a vascular lumen.

Yet another objective of the invention is to produce syringes, especially for the administration of semi-solid formulations, making it possible to ensure that the needle is sterile right up to the very moment of injection.

Some or all of these objectives can be achieved by the various embodiments of the invention.

In a first embodiment of the invention, the subject of the invention is a syringe, preferably prefilled with a dose to be entirely delivered, intended for the parenteral injection of a semi-solid formulation, comprising a hollow element forming a reservoir, for containing the semi-solid preparation to be injected, between a piston and a base of a needle which comes into contact with one end of said element forming a reservoir, for example by being introduced via one end into said reservoir, so that the piston comes into direct contact with said base at the end of the injection of the dose contained in said element forming a reservoir, said element forming a reservoir and said needle being held fastened to each other at said base by a support or casing which houses said element forming a reservoir.

Preferably, said support or casing forming the peripheral shell surrounds, with a small or virtually zero clearance, the external surface of said element forming a reservoir so that the latter may be manufactured with a thin wall and/or of a weak material, without being damaged by the high pressure likely to develop during the injection and compression of the semi-solid formulation.

Preferably, said element, hereafter denoted as reservoir, is cylindrical and introduced and locked inside a hollow body consisting of said support or casing. Thus, it is the casing which provides the protection and the mechanical resistance, especially to pressure, of said syringe.

In one particularly preferred embodiment, said cylindrical reservoir may be a straight hollow tube having constant internal and external diameters.

In this case, it is preferred for the internal diameter of the reservoir to be close to or even equal to that of the internal bore of the needle which extends the reservoir. If the internal diameter of the reservoir is greater than that of the bore of the needle, a uniform conical or funnel-shaped narrowing is advantageously provided toward that end of the reservoir which houses the needle. The cone angle will, for example, be less than 120°.

In general, it is preferred for the cylindrical reservoir of the syringe, which contains the pasty formulation to be injected, to have as small a diameter as possible depending on the necessary volume.

Depending on the viscosity of the semi-solid formulation and its volume, internal diameters of the needle of between 0.2 and 1.2 to 1.5 mm may in particular be envisaged. Preferably, the internal diameter of the reservoir, and therefore the diameter of the piston of the syringe, will also vary between 0.2 and 5 mm. It will then be possible, using a piston stroke having a maximum length of 7 cm, to inject volumes of 1 to 10 µl and up to 0.5 or 1 ml. The external diameter of the reservoir may, for example, be standardized to 6 mm, or 7, thereby allowing the aforementioned various internal diameters to be provided.

In the case of a tubular reservoir, provision may be made for the reservoir to consist of two tubes, one placed in the other so as to increase the resistance to internal pressure.

In another embodiment, such a tubular reservoir may consist of two or more tubes, one placed behind the other and held in this position by the casing, such an embodiment making it possible in particular to facilitate the formation of syringes allowing the administration of different volumes.

Advantageously, the casing may consist of two elements, one of which forms a hollow body into which the element forming a reservoir is introduced and the other of which contains the hollow body and traps the reservoir, one of the elements leaving an opening for passage of a piston rod and the other element leaving an opening for passage of the needle.

In this case, it is preferred for the opening in said second casing element to form a guide for a piston rod having a diameter approximately equal to the internal diameter of the reservoir.

This second element may also include gripping means or finger rests.

Depending on the case, the injection may be carried out using the force of one's finger or of the palm of one's hand, by providing a gripping area on the first or the second casing element, in order to allow the operator's hand, acting on the end of the piston rod, to push the piston right into the casing.

As a variant, means may be arranged, on said first or second element, so as to gear down the injection force or to replace the manual force with a means of mechanical or driving assistance or any other driving means, especially a gas, spring or electromechanical means.

For example, the opening in said second element may advantageously be threaded in order to engage with a thread on the piston rod so as to allow helical movement of said rod.

As a variant, said second element may have a peripheral thread onto which an internally threaded bush having a central piston rod can be screwed.

In one particularly advantageous embodiment of such a device, said element forming a reservoir and the needle are assembled, at a needle base, without any bonding, clip-fastening or any other positive assembly means, ensuring assembly, and resistance to the forces tending to disassemble its components, by means of said casing, said casing being designed to prevent axial separation of the reservoir from the needle.

Such an embodiment may also facilitate the separation of the elements of the syringe by disassembly after use.

The piston, which may or may not be fastened to a piston rod, preferably has a shape which matches the base of the needle or that end of the reservoir on the same side as the needle so as to leave as small an unused volume as possible when the piston reaches its end-of-injection position. If the syringe has a frustoconical or funnel-shaped end, the piston advantageously has a complementary shape.

Furthermore, as soon as a constant diameter and constant length of the reservoir tube and, possibly, of a needle base part intended to be clamped between the reservoir tube and a casing element have been defined, the same casing can be used for reservoirs provided for the entire range of formulation doses.

One embodiment of the syringe according to the invention, in which the support or casing provides the functions of reinforcing the reservoir against the internal pressures and/or of clamping the needle base against the reservoir, may advantageously and beneficially be used to solve the sealing problems either by not using a seal, for example between the base and the reservoir or between the piston and the reservoir, or by attaching a seal at a certain distance from the semi-solid formulation, the narrow interstice between the wall of the reservoir and the base or the piston causing, in addition, only a negligible loss of the formulation. Advantageously, the base of the needle and the piston will then be made of the same material, and preferably of the same material as the needle, for example stainless steel, while at the same time ensuring that, in order to preserve the formulation, a sealing is provided during preservation and storage and during injection. Thus, for example, contact between the formulation and the syringe may be virtually or completely limited to stainless steel if all the constituents—reservoir, base and piston—are made of this metal, or of glass and steel if the reservoir is made in the form of a glass tube.

Preferably, the base of the needle and the piston are made of the same material, for example stainless steel.

Preferably, in order to avoid the risk of injection into a vessel, a device for injecting a semi-solid formulation, especially such as an aforementioned device according to the invention, will include means which make it possible to check whether any blood has been withdrawn from a vessel, this being achieved without having to pull on the piston as is done in the case of liquid formulations.

A first, non-preferred, solution will consist in fitting a catheter needle on the device, that is to say a needle intended for a parenteral passage and containing, in its bore, a second needle for the injection proper, the space between the two needles allowing blood to be withdrawn by the capillary effect as far as a region open to the outside. This solution is not preferred since it increases the diameter and the length of the needle.

Advantageously, the device has a passage, comprising a region visible to the operator, which communicates with the internal bore of the needle and allows, by capillary effect or vacuum or the intravascular pressure, blood to be seen should the needle have penetrated a vascular lumen.

In the case in which the blood can be withdrawn under its own pressure or by capillary effect, provision is made for the internal bore of the needle to communicate with the external atmosphere via a path providing a pressure drop such that a flow of blood is allowed but that any substantial flow of the semi-solid formulation is unable to take place.

In such an embodiment, a small-diameter hole, for example having a diameter of less than 0.3 mm, may be made in the wall of the actual needle, making it possible to see that blood has been withdrawn. However, this solution is not preferred as it is difficult to realize.

In a second embodiment, the passage for the blood from the needle may pass into a chamber provided in the reservoir and include an elongate pressure-drop path, preferably a helical one, for example lying between a thread on the base of the needle and a complementary surface in the transparent wall of the reservoir or vice versa, this thread terminating, where appropriate, in a blood display region, this thread communicating, at its end, directly or through the display region, with the external atmosphere via a small-diameter hole.

In another highly advantageous embodiment, the inside of the needle and of the syringe is maintained under vacuum and a withdrawal of blood will, by pressure difference, emerge in a display region, which display region may, moreover, be designed in the form of the aforementioned thread or comprise such a thread, communication with the atmosphere then not being provided.

In an advantageous embodiment, the needle may be covered by a cap, a package or another retractable, deformable or foldable protective element which isolates it from the outside and which will be transpierced by the needle at the moment of injection, whilst moving away over at least most of, and preferably the entire, length of the needle during its parenteral penetration.

Such a transpierceable protection element can allow the inside of the syringe to be maintained under vacuum. When the operator presses the syringe, provided with its protection element, against the skin and pushes in the piston, the needle transpierces the protection element and penetrates the epidermis without a substantial loss of vacuum, so that, in the event of penetration into a vascular lumen, the blood will be withdrawn into the needle and brought to a display region as described above.

This package may consist, for example, of a tube or a sachet made of plastic sealed around the needle or onto the latter.

Such a very thin package, which completely isolates the needle from the outside, may optionally be sealed at the end of the needle, for example by heat sealing, so as to completely close off the end or the bevel of the needle in the manner of a plug, in which case, the device can also be used for conventional liquid injections.

If it is desired to see a possible withdrawal of blood, being withdrawn by capillary effect, provision may be made for the hole connecting the pressure-drop passage to the external environment to emerge, in fact, inside this package so that no communication actually exists between a non-sterile atmosphere and the inside of the needle.

If the package or protection element is formed by an extremely flexible and therefore fragile tube or sachet, a removable rigid cap may be provided for general protection, said cap being placed on top of this package or protection element.

Another function of such a package or protection element may be to permit a vacuum to be maintained in the syringe, for vacuum packaging of the formulation in the reservoir in non-hydrated form, it then being possible for the hydration to be carried out subsequently by pushing the needle into a reservoir, pouch or carpule containing the liquid injection medium, so as to put the desired volume of liquid back into the formulation and to ensure that the formulation is obtained in semi-solid form.

Particularly preferably, the reservoir is prefilled before the various elements forming the syringe are mounted and, particularly advantageously, this prefilling may be such that the volume of formulation occupies the entire space between the piston and the needle without it being necessary to purge the syringe before injection. Depending on the viscosity of the pharmaceutical substance, it may even be necessary to avoid the conventional hand movement which consists in withdrawing the piston in order to create a suction and thus to check the injection site. This would have the effect of creating a cavitation in the substance, leading to the risk of inhomogeneous deposition of the substance. In this case, a piston rod is used which is not connected to the piston.

This filling may be carried out, depending on the types of formulation, either directly with the semi-solid formulation or with a formulation capable of assuming a semi-solid state, for example a formulation formed from a powder and from a liquid allowing a semi-solid paste to be formed, these being introduced simultaneously or sequentially into the reservoir.

Advantageously, the filling may be carried out by a process in which a filling nozzle is connected at one of the ends of the tube or reservoir, temporarily plugged by the piston or by a septum, said piston or septum then being displaced during filling of the formulation, said tube or reservoir then being plugged by the base of the needle being placed over said end.

This will make it possible in particular to use the same process and the same filling device, whatever the semi-solid formulation.

The invention also relates to processes for administering semi-solid formulations by parenteral injection using a device according to the invention.

In such a process it is preferred, after the needle has been injected, to wait a few moments before expelling the semi-solid formulation in order for the injection site to be confirmed by there being no withdrawal of blood.

BRIEF DESCRIPTION OF THE DRAWINGS

Further advantages and features of the invention will appear on reading the following description, given by way of non-limiting example and with reference to the appended drawing in which.

DETAILED DESCRIPTION OF THE PREFERRED EMBODIMENTS

Figure 1:
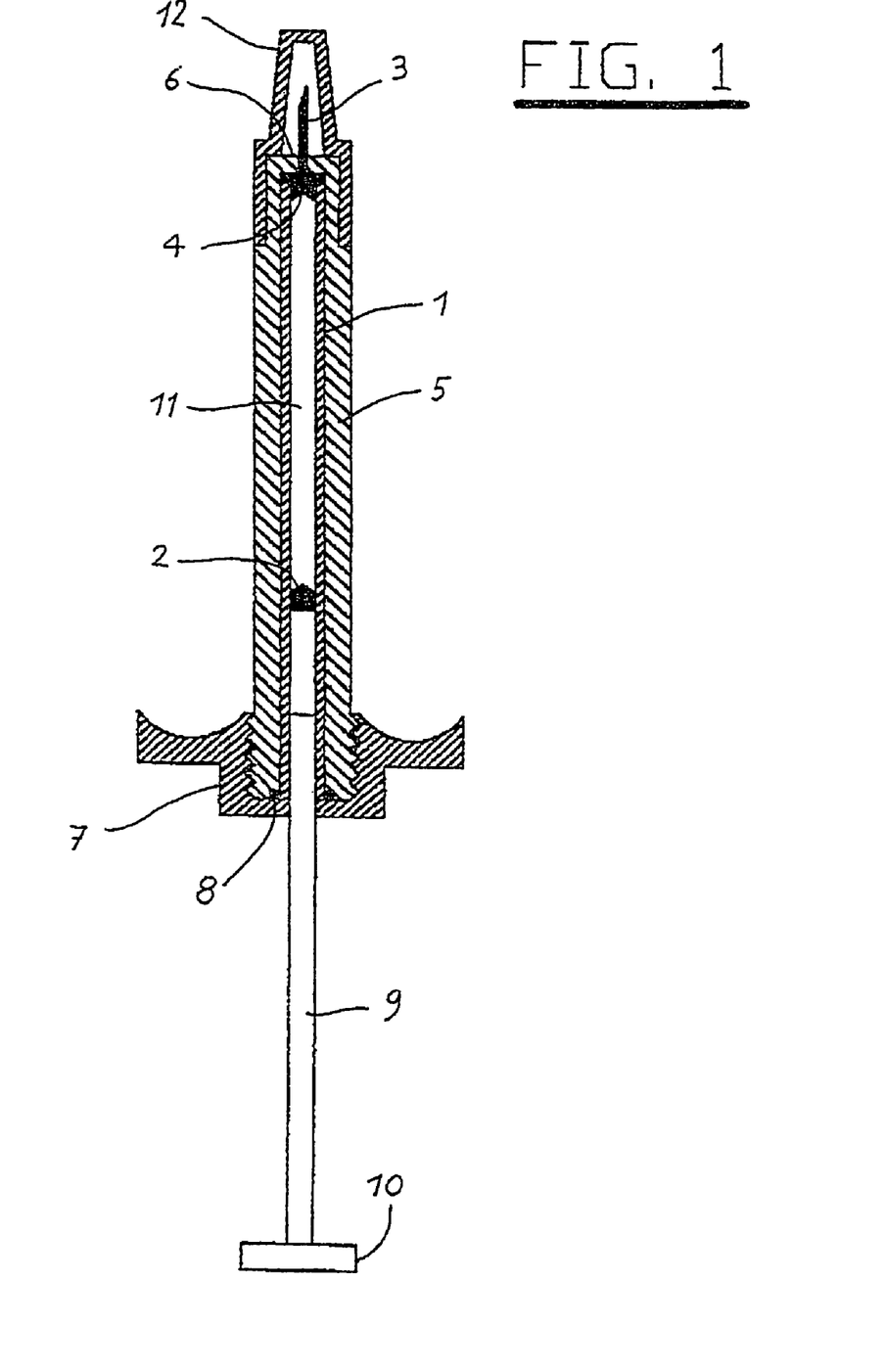
FIG. 1 shows a schematic view in longitudinal section of a syringe according to a first embodiment of the invention with the piston rod extracted.

FIG. 1 shows a syringe for the administration of a semi-solid formulation, comprising a casing element 1 in the form of a tubular piece, for example made of glass or polyethylene or polypropylene plastics, of cylindrical shape with a circular cross section, in which a piston 2 can move. The needle 3, of conventional type, is fastened to a base 4 having, at the point where the needle penetrates the base, a radial flange followed by narrower cylindrical part. The bore of the needle has not been shown. The base 4 is pushed into the end of the reservoir tube 1 until its flange presses against the end of the tube. It is known that the base, which is seen in cross section in the figure, has, near the piston 2, a concave frustoconical shape complementary to the convex conical end of the piston 2 in order to promote the flow of the fluid, particularly if it is viscous, so that at the end of injection the piston 2 closely matches the base and thus limits any dead volume. The assembly comprising the reservoir tube 1 and the needle 3 with its base 4 is pushed into a first casing element 5 of tubular shape, the front end 6 of which is closed and provided with a central passage having a diameter greater than that of the needle 3. The length of the casing element 5 may be such that, when the assembly 1+3 is pushed into the element 5, the rear end of the tube 1 emerges very slightly beyond the lower end of the piece 5.

The casing includes a second casing element 7 in the form of a cup which is provided with a central passage having a diameter approximately identical to the internal diameter of the tube 1 and which has lateral tabs or finger rests. The piece 7 is, for example, screwed onto the element 5 by means of complementary threads and it will be understood that at the end of screwing the rear end of the tube 1 presses against the bottom of the cup 7 while its front end clamps the flange of the base 4 against the bottom 6 of the casing element 5, as well as the seal 8 which makes it possible to guarantee that the assembly, once assembled, is aseptic, so that the needle and the reservoir are axially immobilized one with respect to the other and cannot move.

This seal 8 may be placed, as in FIG. 1, so as to prevent any passage into the interstice between the tube 1 and the body 5, or else, on the contrary, between the base 4 and the corresponding end of the tube 1, asepsis of the interstice between the tube 1 and the body 5 then no longer being necessary.

A piston rod 9 terminating in a bearing surface 10 is pushed into the assembled syringe until the front end of the rod 9, the diameter of which is preferably slightly less than the internal diameter of the tube 1, bears against the piston 2. If, thereafter, the rod 9 is pushed in, it pushes back the piston 2, without being fastened thereto, and the formulation which is contained in the volume 11 located between the piston and the base can thus be expelled.

A removable cap 12 may be provided for sterility.

Advantageously, the syringe just described may be prefilled. This prefilling may be carried out using a formulation which is already in the semi-solid state obtained, for example, by mixing a powder of active principle and a liquid, allowing a paste to be formed. The filling may also be carried out using a dry powder which could be rehydrated to the pasty state extemporaneously before injection, as described in French patent application No. 96/06886.

The prefilling is preferably carried out in the following manner. The tubular reservoir 1, in the disassembled state, receives the plug 2 positioned in its upper end, that is to say the end which will house the base 4. This end is placed so as to face a nozzle for delivering the pasty formulation. The nozzle delivers the desired volume of the formulation, thereby progressively pushing the piston 2 back into the tube until it reaches the final position in which the pasty formulation completely fills the volume 11. Next, the base 4 is pushed into this end and the assembly is fitted into the body 5, 7.

Optionally, the tube has been packaged beforehand in a package and is sealed upon insertion into the hollow body or casing which carries the needle and its cap, the assembly being held together in a second package.

It will be understood that a syringe has thus been produced which is capable of storing and then injecting a semi-solid formulation, which syringe consists of very simple and reasonably priced elements compared with conventional syringes. The materials used may be made of plastic, glass or metal. All the elements of the syringe are assembled without any bonding or clip-fastening or screwing likely to cause problems of residues in contact with the formulation. Furthermore, the syringe can be completely dismantled after use.

Depending on the semi-solid formulation and its volume, this syringe can be used manually without any mechanism for gearing down the force. Thus, up to a maximum force of 50 N and preferably less than 30 N, injection may be carried out manually by moving the rod 9 by pressing on the end 10 with one's thumb.

If, depending on the hardness of the product, on the volume to be injected or on the diameter of the needle, the forces needed exceed 30 or even 50 N, the syringe according to the invention may advantageously be provided with an assistance device.

Figure 2:
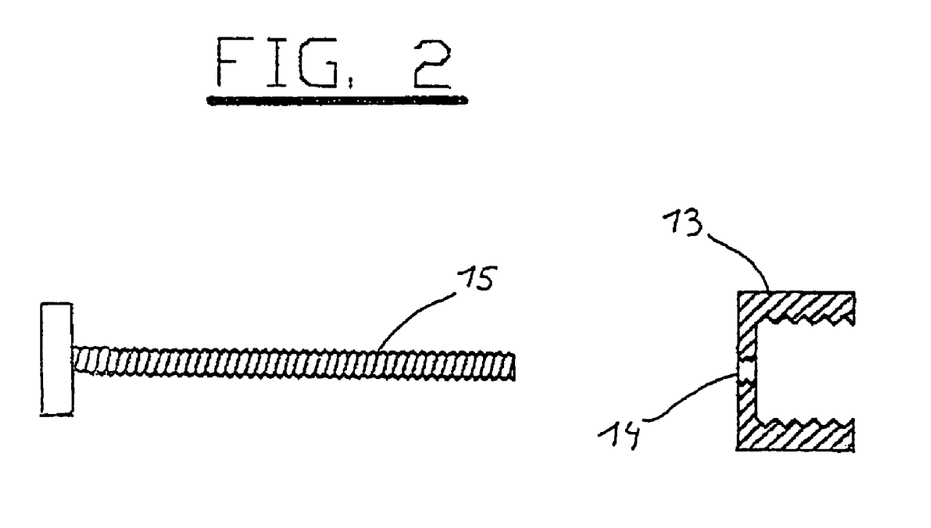
FIG. 2 shows a schematic view of a rear casing component and of a threaded piston rod according to a variant of the invention.

FIG. 2 shows that the piece 7 need only be replaced with a cup-shaped piece 13 which can be screwed in the same way onto the end of the casing element 5 and which is provided with a tapped passage 14 into which a threaded piston rod 15 can be screwed. All that is then required is to rotate the threaded rod 15 in order for it to move in the tube 1 and, consequently, for the thrust of the piston 2 to expel the formulation. Such gearing-down can easily allow forces of the order of 200 N to be deployed. Moreover, the screw pitch also makes it possible to administer only part of the dose, and in a precise manner by virtue of a graduated scale.

It will furthermore be understood that, as long as the two casing elements 5 and 7 or 13 are made of a sufficiently strong material, the tube 1, the piston 2 and the base 4 can withstand very high pressures without any appreciable deformation or rupture.

Figure 3:
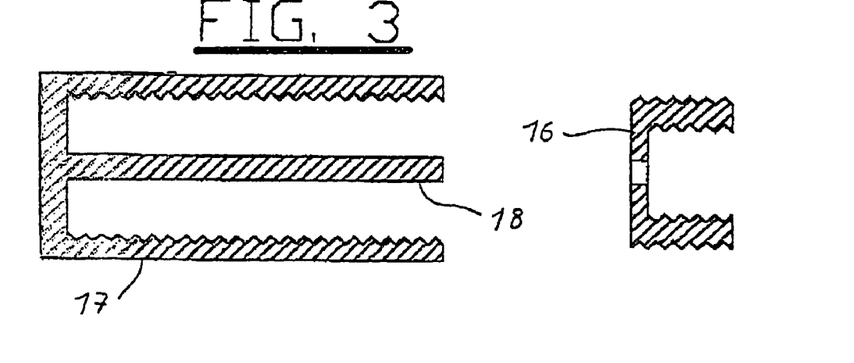
FIG. 3 shows a schematic sectional view of another arrangement of a piston rod and of a rear casing component.

FIG. 3 shows another form of gearing-down in which the second casing element 16 has a non-threaded hole and an internal thread capable of being screwed on the external thread of the casing element 5 and a second external thread onto which an internally threaded element 17 in the form of a bush or sleeve can be screwed, said bush or sleeve being provided internally with a cylindrical rod 18 acting as piston rod. Screwing the element 17 onto the external thread of the element 16 causes the element 17 to move, with pushes back the piston and ensures injection and precise metering by millimetric movement and a corresponding graduated scale.

Figure 4:
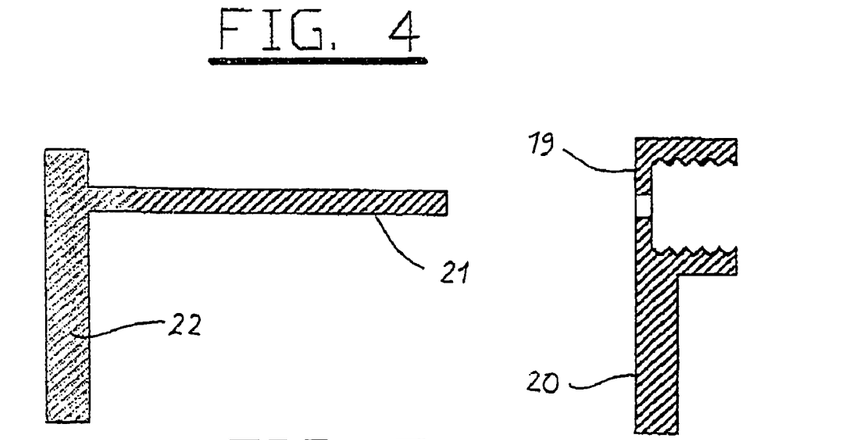
FIG. 4 shows a schematic sectional view of another arrangement of a piston rod and of a rear casing component for gearing down the force.

FIG. 4 shows a device in which the second casing piece 19, very similar to the piece 13, has a lateral arm 20, while the piston rod 21 also terminates in a lateral arm 22, it being possible for the two arms 20, 22 to be gripped by the user's hand in order to deploy all the force of his hand.

Figure 5:
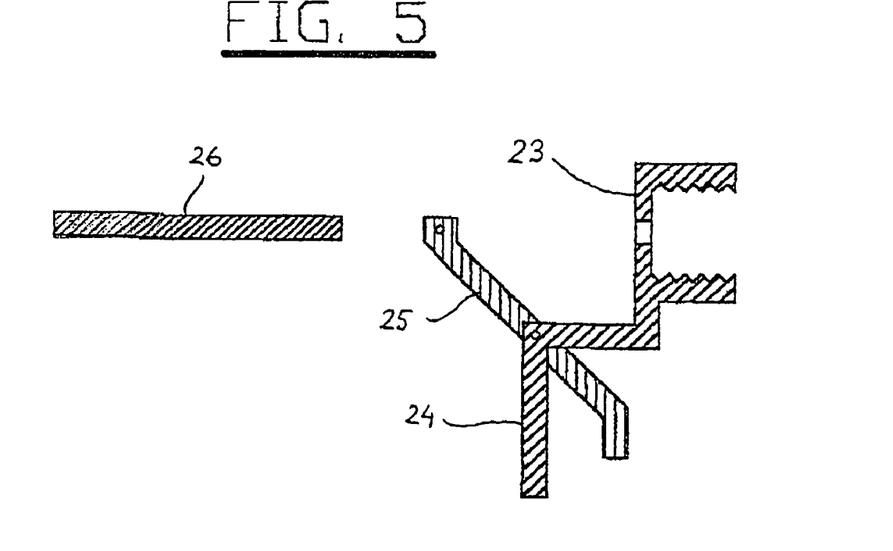
FIG. 5 shows a schematic sectional view of another arrangement of a rear casing component and of a piston rod, the piston rod being shown separated from the lever mechanism.

FIG. 5 shows schematically a second casing element 23 provided with a rearwardly-shifted lateral arm 24, to which a lever 25 is hinged, one end of which allows it to be gripped in the hand, simultaneously with the part 24, and the other end of which is hinged to the piston rod 26, so that it is possible for the necessary force to be geared down by the lever effect.

The syringe shown in FIG. 1 can accommodate different volumes of semi-solid formulation, which volumes will be manifested by a different position of the piston 2 at the end of the preloading of the formulation. When the volumes to be injected become even smaller, it is possible, without modifying the casing 5, 7, to use tubes 1 having the same external diameter but having a smaller internal diameter, the bases 4 and pistons 2 then being modified.

Figure 6:
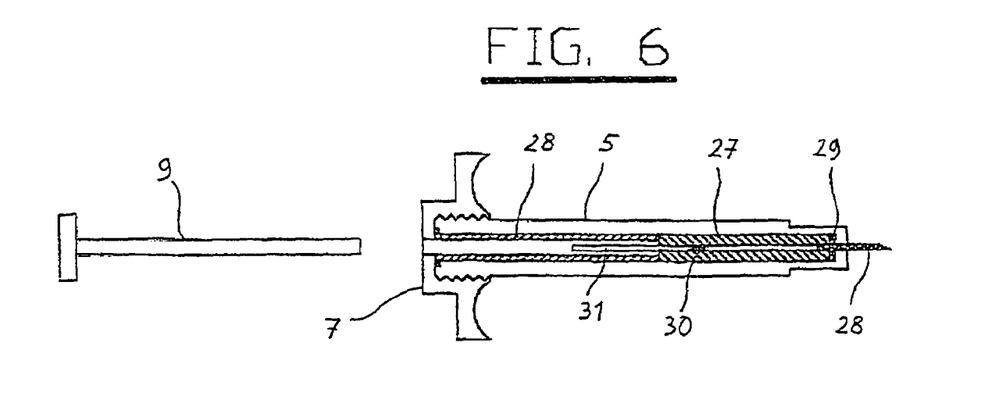
FIG. 6 shows a schematic sectional view of a syringe according to another embodiment, comprising two consecutive tubular elements.

FIG. 6 shows another embodiment allowing the injection of small volumes. In this example, the internal volume of the casing element 5 is occupied not by a single tube, but by an assembly of two consecutive tubes, the first, namely a reservoir tube 27, having a very small diameter and being extended by the needle 28 with its base 29. A small-diameter piston 30 can move in this tube 27 under the thrust of a rod 31 emerging to the rear of the tube 27. The tube 27 is juxtaposed with a second tube 28 having the same external diameter but a larger internal diameter, in which tube 27 the piston rod 9 can move. The piece 7 holds the tubes 25 and 28 in contact with each other and provides the cohesion of the assembly, as in the syringe shown in FIG. 1.

Figure 7:
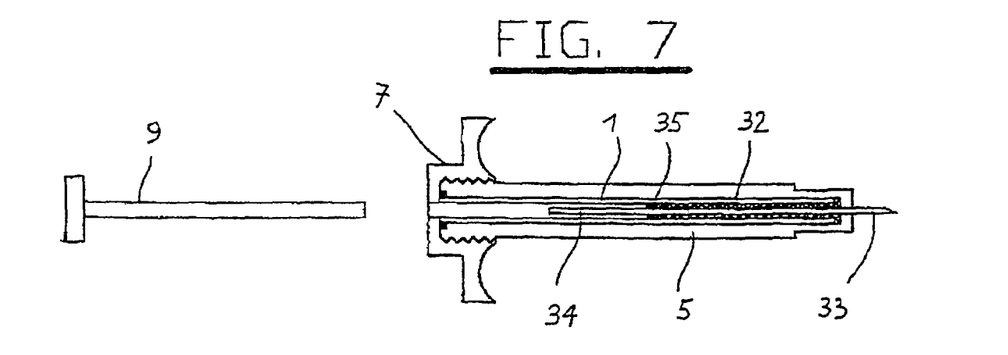
FIG. 7 shows a schematic sectional view of another embodiment of the invention, comprising two concentric tubular elements.

FIG. 7 shows another embodiment in which, in order to have a small volume of formulation using a large-diameter tube 1, it is the base 32 of the needle 33 which extends over a great distance inside the tube 1 in order to form the reservoir proper, filled with the preloaded formulation. The piston may, for example, be made in the form of a metal rod 34 emerging in the tube 1 and passing through a septum 35 which holds it in place.

The embodiments described in FIGS. 6 and 7 also lend themselves particularly well to the production of reservoirs of which the internal diameter is equal to that of the bore of the needle or slightly different, for example slightly greater.

It is also conceivable for the reservoir and the needle to consist of a single tubular piece terminating in a bevel at the end of the needle and being able to be penetrated by a small-diameter rod forming a piston. In this case, the piston is preferably designed so that, at the end of travel, that is to say at the end of injection, it reaches close to the free front end of the needle so as to leave virtually no volume of formulation inside the needle.

Figure 8:
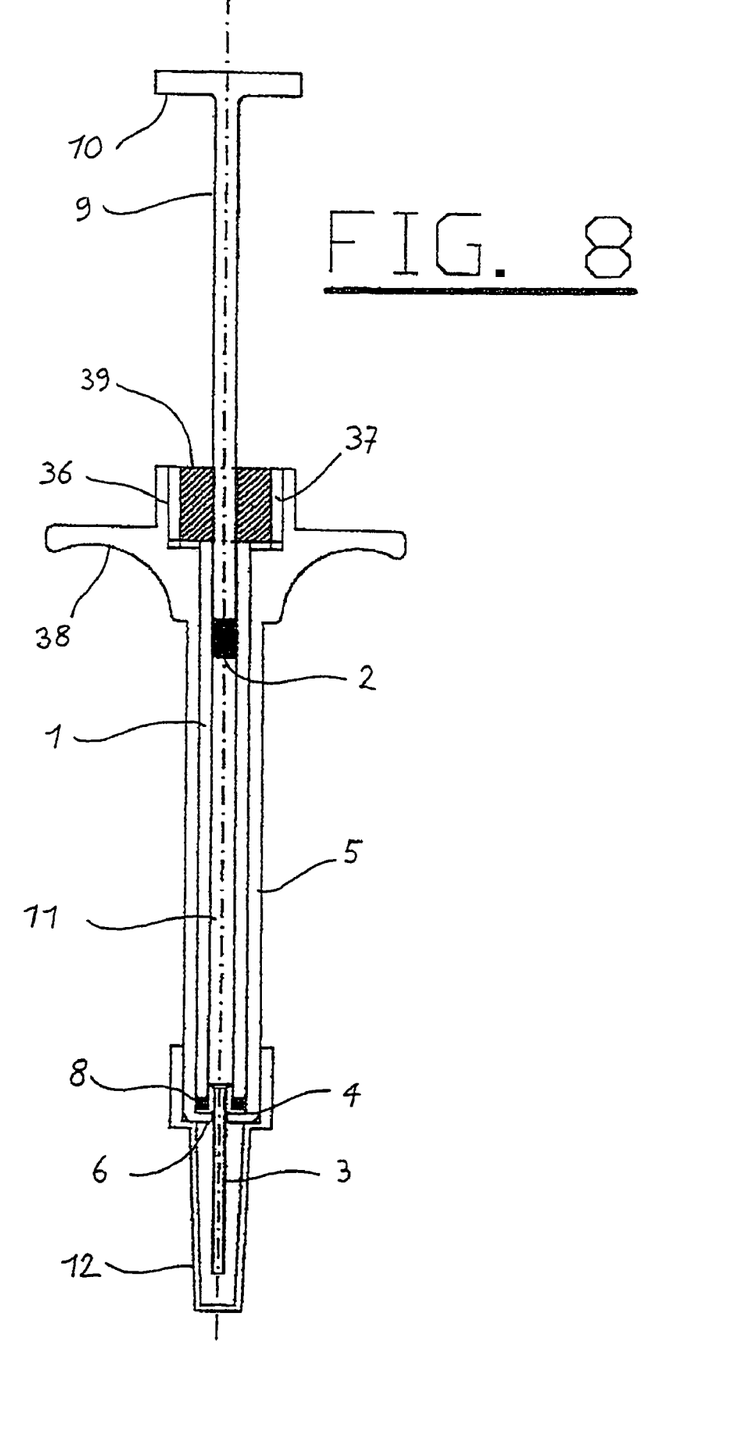
FIG. 8 shows a more detailed sectional view of a syringe according to one embodiment of the invention.

FIG. 8 shows a detailed embodiment of a syringe according to FIG. 1.

However, in this embodiment the second casing element has no piece 7. More specifically, a ring 36 is fixed to the external thread 37 of the piece 5 and has the finger rests 38. The tube 1 is held in position by a plug 39 fixed in the end of the piece 5 by screwing or "clip-fastening".

Figure 9:
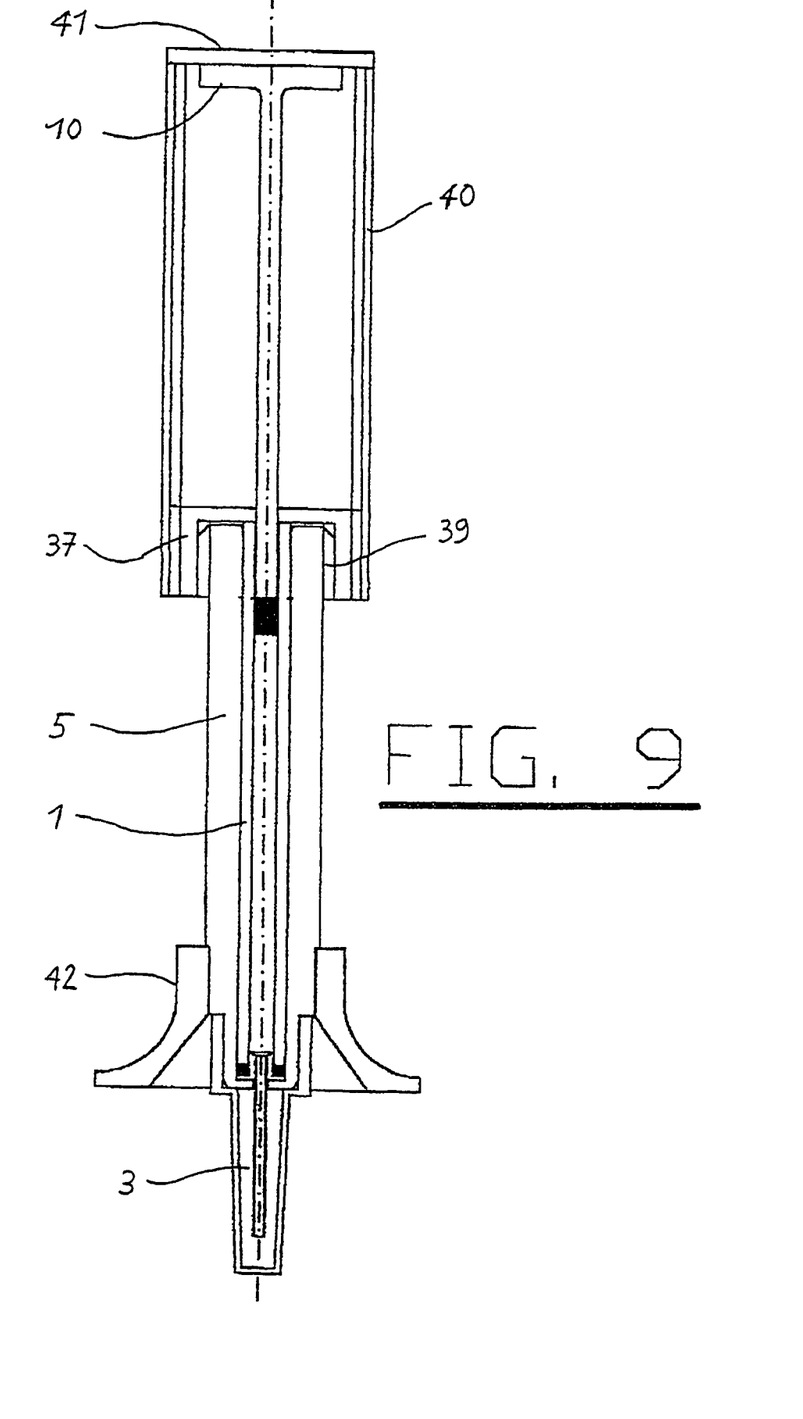
FIG. 9 shows a more detailed sectional view of another embodiment of such a syringe equipped with an optional means of gearing down the force.

FIG. 9 shows a device similar to that in the previous figure, but in which the piece 36 is omitted. Instead of the piece 36, an internally threaded bush-shaped piece 40 may be screwed onto the thread 37 of the element 5, the bottom 41 of which bush-shaped piece 40 can press against the end 10 of the piston rod 9, which may be seen in various positions, when the bush 40 is screwed onto the thread so that this screwing movement causes the piston to advance and the semi-solid formulation to be injected. The screw threads will be made so that the injection time does not exceed, for example, 30 seconds. In this case, it should be noted that the seal is located between the base 4 and the reservoir 1. Clamping the assembly must ensure compression of the seal, and therefore asepsis. Given the longitudinal imprecision in the reservoir (glass), a force-measuring screwing mechanism is preferred.

Advantageously, a finger rest or another gripping means 42 may be provided, this time on the front end of the body 5 in order to stabilize the device during injection.

In order to avoid the risk of injection into a vessel, a device for injecting semi-solid formulations, comprising a reservoir, a needle and a piston, according to the invention may be made so that the injection area can be checked without having to pull the piston back rearwards in order to create a vacuum and run the risk of cavitation.

Figure 10:
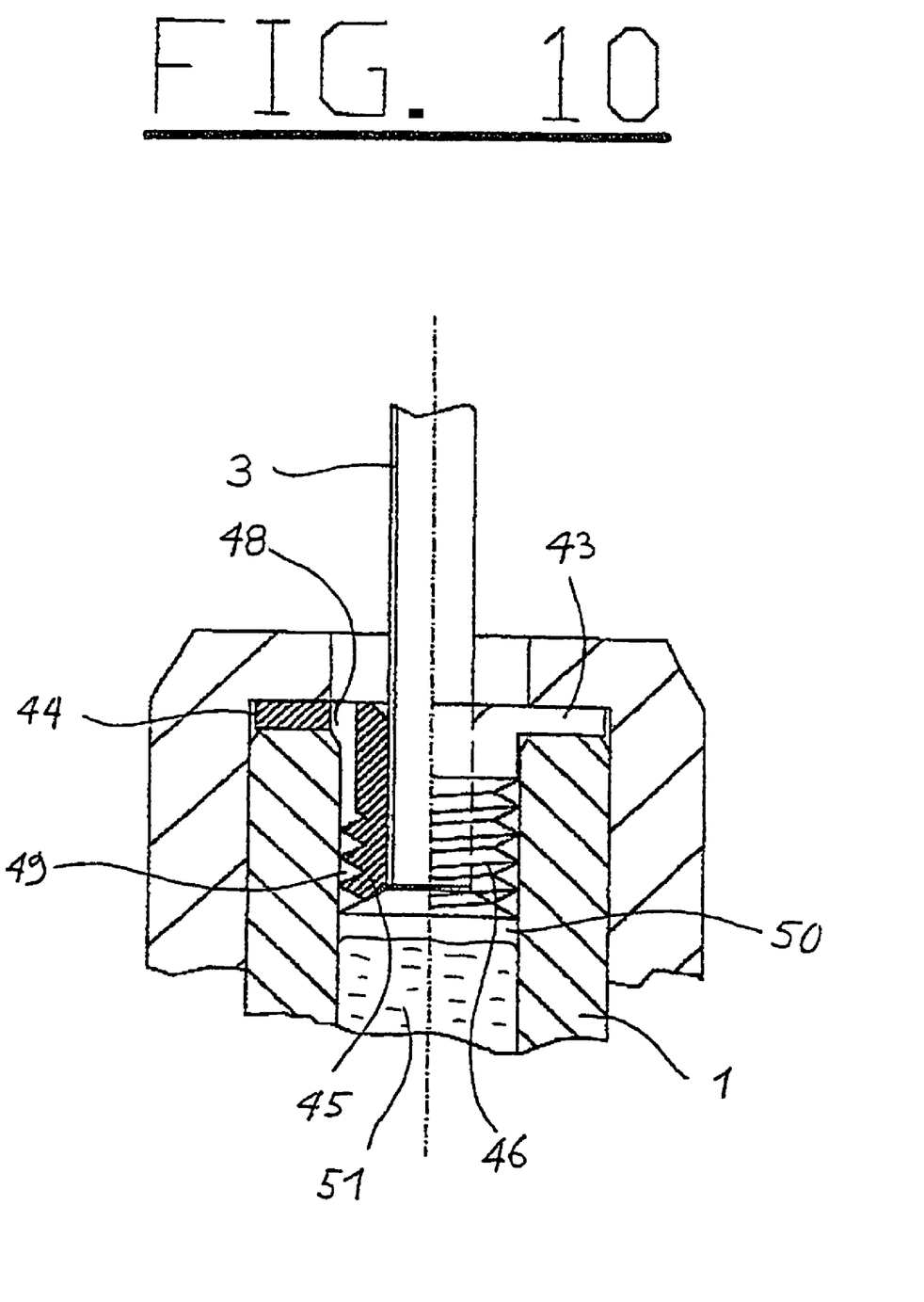
FIG. 10 shows a partial sectional view of a front syringe part according to the invention, intended to allow withdrawal of liquid blood for display.

FIG. 10 shows an embodiment of a needle base allowing this result to be achieved.

The base 43, which houses the needle 3, has, like the base 4, a peripheral flange 44, which bears on the end of the tube 1, and an extension 45, which penetrates the tube, that end of the extension 45 which faces the transparent tube 1 having a conical shape corresponding to the taper of the front end of the piston, allowing the flow to be optimized. This extension 45 has, on its surface, a thread 46 or a helical groove allowing a free volume between it and the corresponding internal surface of the tube 1, or vice versa. A hole 48 brings the volume 49 formed by this helical passage into communication with the open air. It will be understood that, in this way, the inside of the tube 1 communicates with the open air via the hole 48 and the free helical volume 49 bounded by the thread 46 and which produces an elongate path with a controlled pressure drop. Communication with the internal bore of the needle 3 may be provided, for example, by leaving a small free volume 50 between the pasty formulation 51 and the base 43, or it could be provided by a hole through a base part bringing the internal end of the thread 46 into communication with the internal volume of the needle.

Since the tube 1 and the body 5 are made of transparent materials, it will be understood that, if the needle penetrates a vessel, blood will be withdrawn via the bore of the needle because of the intravascular pressure, expelling and replacing the air contained in the volume 50, the helical passage of the thread 46 and possibly the volume 47, which in turn will allow the arrival of liquid blood to be seen over a large area.

When the formulation is pushed back by the piston, in order to be injected, a small amount can penetrate the helical interstice of the thread but is rapidly stopped by the pressure drop that the small flow section and the long length of this interstice represent.

Reference will now be made to FIGS. 11 to 15.

In the field of syringes, it is conventional to surround the needle with a removable cap which protects the needle both in the sterile package and when the syringe is to be used. However, there is no longer any way of protecting the sterility of the needle during the time from fitting the cap to injection. This problem can be solved for the semi-solid-formulation syringes described above, or for any other type of syringe, by providing, around the needle, a flexible package fixed, preferably in a hermetically sealed manner, to one element of the syringe, for example the base of the needle or the front part of the element forming a reservoir, and capable of being pierced by the needle at the start of injection and then of being retracted or compressed as the needle advances into the tissue of the injection area.

Preferably, this shroud leaves a very small space between it and the needle.

Particularly preferably, the inside of the needle and the volume in which it emerges in the syringe reservoir are maintained under vacuum by virtue of the presence of this needle shroud, the inside of which is under vacuum.

This makes it possible to provide a suction effect which, if the needle penetrates a vessel, rapidly withdraws liquid blood into the needle and then into a display area designed for this purpose.

Figure 11:
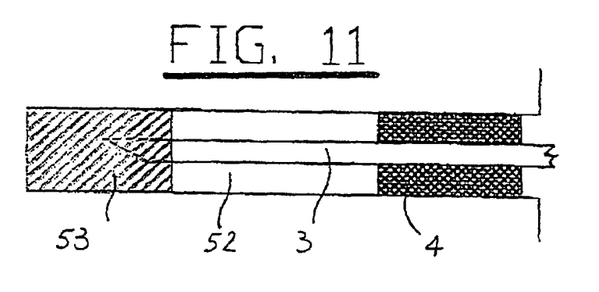
FIG. 11 shows a schematic view of a needle of a syringe according to the invention, with a tubular shroud.

Referring more particularly to FIG. 11, this shows a thin plastic tube 52 which is sealed at one end to the internal face of the base 4 and which surrounds the needle 3 starting from this face, this tube itself being sealed in the region 53 which surrounds the tip of the needle.

In a variant, this tube 52 may be removed in order to free the needle. However, in another variant, this tube may be designed so as to deform and be retracted if the syringe is pressed against the patient's epidermis so that its end 53 is transpierced by the needle.

Figures 12, 13:
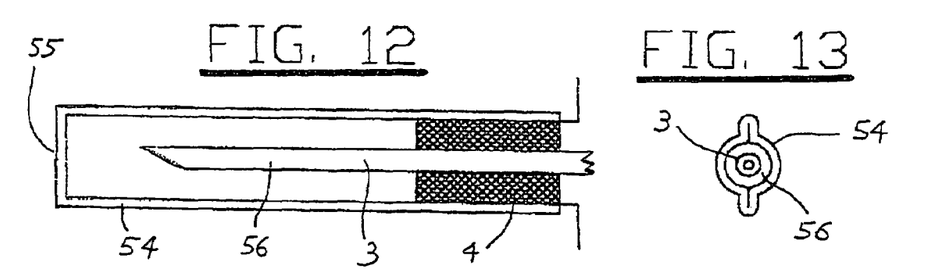
FIG. 12 shows a schematic view of a front end of a syringe according to the invention, with a shroud in the form of a sachet.
FIG. 13 shows a cross-sectional view of the needle and of the shroud in FIG. 12.

FIGS. 12 and 13 show more particularly that, instead of such a tube closely surrounding the needle, a very thin plastic sachet 54 may be provided, one end of which surrounds the base 4 in a hermetically sealed manner, which sachet 54 is closed off at its other end 55, it being possible for this sachet to have, for example, the sectional shape shown in FIG. 13, leaving a very small volume 56 between the needle 3 and the sachet itself.

Preferably, the inside of the syringe and therefore the inside of the sachet and the volume 56 is packaged under vacuum.

Figure 14:
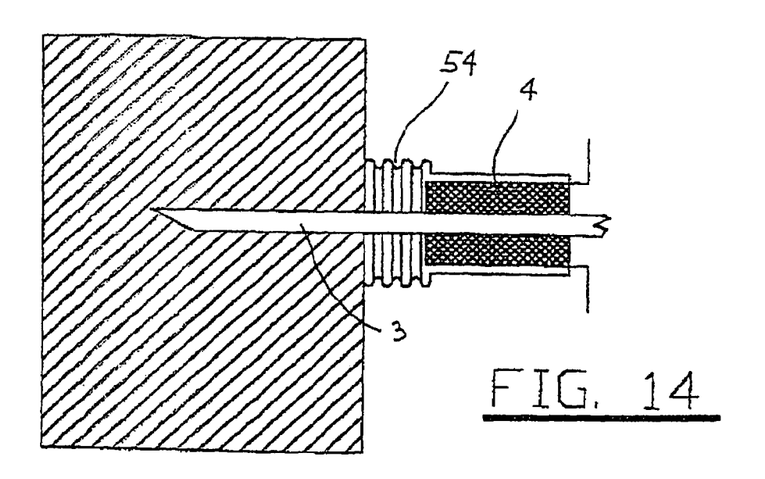
FIG. 14 shows a schematic view of the needle and of the shroud in FIG. 12, during injection.

When carrying out the injection, as may be seen in FIG. 14, the bottom 55 of the sachet is transpierced by the tip of the needle 3 and the advancing of the needle causes the sachet 54 pressed against the epidermis to retract. It may estimated that the passage of the needle through the sachet, in order to penetrate the skin, ought not to break the vacuum so that, if the needle penetrates a vessel, the blood is sucked up through the needle and ends up in a display region, for example in a volume left free between the outlet of the needle in the reservoir and the dose of semi-pasty formulation, or in any other visible region communicating with the inside of the needle, for example a region similar to the region 49, but without the presence of a hole such as 48, since this region must not be in communication with the atmosphere.

Figure 15:
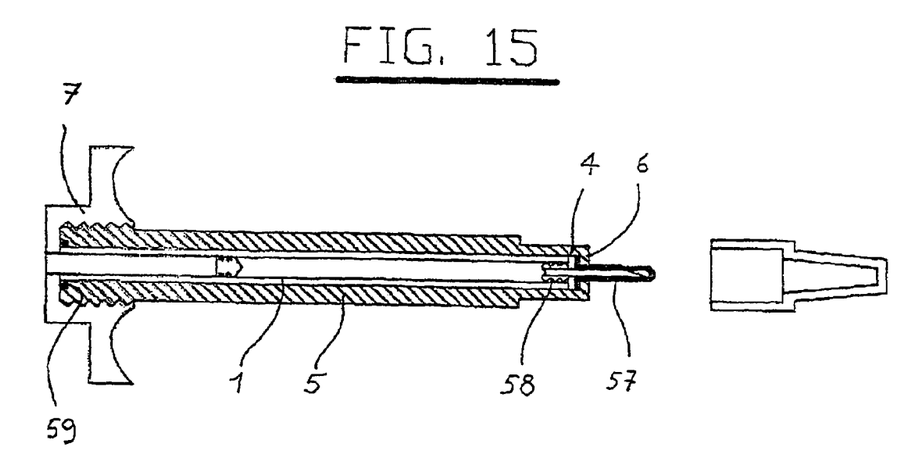
FIG. 15 shows a schematic sectional view of another embodiment of the invention, with a needle-protecting shroud.

FIG. 15 shows schematically a syringe according to the invention in which a needle package 57, made of a flexible, preferably and bendable plastic surrounding the needle, is clamped in a hermetically sealed manner against the bottom 6 of the syringe body 5 by the flange of the base 4, this base having, in the part which enters the reservoir tube 1, a thread 58 similar to the thread 46 but not opening to the atmosphere. The assembly is held in place by a structural piece 7 with the interposition, around the rear end of the tube 1, of an annular seal 59 which completes the vacuum sealing between the tube 1 and the casing 5.

What is claimed is:

1. A prefilled syringe configured for the parenteral injection of a semi-solid formulation, comprising:

a longitudinally continuous hollow element forming a reservoir, prefilled with a semi-solid preparation to be injected;

a piston having a convex tip for pressing against the semi-solid preparation to be injected;

a needle at one end of said hollow element, said needle having a supporting base, said semi-solid preparation being between said convex tip and said supporting base of said needle, said supporting base directly contacting an entirety of one end face of said hollow element, so that when the piston comes into direct contact with said base of said needle, an entire dose contained in said reservoir is injected; and a casing which houses said hollow element and provides mechanical resistance of the syringe, said hollow element and said needle being held fastened to each other at said base of said needle by said casing, wherein said casing forms a peripheral shell surrounding an external surface of said hollow element so that an internal surface of said casing directly contacts said external surface of said hollow element along an entirety of said external surface, and wherein said casing axially forces said hollow element directly against said base of said needle and strengthens said hollow element against radial pressures generated by said axial forces and generated by the ejection of said semi-solid formulation.

2. The syringe as claimed in claim 1, wherein the reservoir is cylindrical and introduced and locked inside a hollow body consisting of said casing, which provides the protection and the mechanical resistance of said syringe.

3. The syringe as claimed in claim 2, wherein said cylindrical reservoir is a straight hollow tube having constant internal and external diameters.

4. The syringe with a tubular reservoir as claimed in claim 3, wherein the tubular reservoir consists of two or more tubes, one placed behind the other, which are held in this position by the casing, for facilitating the formation of syringes allowing the administration of different volumes.

5. The syringe as claimed in claim 4, wherein means are arranged, on one of said first and second elements, so as to gear down the injection force or to replace the manual force with a means of mechanical or driving assistance.

6. The syringe as claimed in claim 5, wherein the opening in said other element is threaded in order to engage with a thread on the piston rod so as to allow helical movement of said rod.

7. The syringe as claimed in claim 5, wherein said other element has a peripheral thread onto which an internally threaded bush having a central piston rod is screwed.

8. The syringe as claimed in claim 3, wherein the internal diameter of the reservoir is close to or even equal to that of the internal bore of the needle which extends the reservoir.

9. The syringe with a tubular reservoir as claimed in claim 3, wherein the reservoir consists of two tubes, one placed in the other, so as to increase the resistance to internal pressure.

10. The syringe as claimed in claim 1, wherein the needle is covered by a cap, a package or other flexible protection element which isolates the needle from the outside and which will be transpierced by the needle at the moment of injection, this cap, package or protection element being one of retractable, deformable and foldable in order to move away during penetration of the needle and to permit penetration of all or most of the length of the needle.

11. The syringe as claimed in claim 10, wherein said package consists of a tube or a sachet made of plastic, sealed around or onto the needle.

12. The syringe as claimed in claim 11, wherein said package, which completely isolates the needle from the outside is sealed at the end of the needle so as to completely close off the end of the needle in the manner of a plug.

13. The syringe as claimed in claim 10, wherein an inside of the syringe is under vacuum.

14. The syringe as claimed in claim 10, in which any withdrawal of blood, being withdrawn by capillary effect, may be seen, wherein the hole connecting the pressure-drop passage to the external environment emerges, in fact, inside this package so that no communication actually exists between a non-sterile atmosphere and the inside of the needle.

15. The syringe as claimed in claim 10, wherein said cap, package or protection element is fixed to a front end of the reservoir.

16. The syringe as claimed in claim 1, further comprising a passage, comprising a region visible by the operator, which communicates with the internal bore of the needle and allows, by one of pressure, capillary effect and vacuum, blood to be seen should the needle have penetrated a vascular lumen.

17. The syringe as claimed in claim 16, wherein the inside of the needle and of the reservoir is maintained under vacuum so that a withdrawal of blood will, by pressure difference, emerge in a display region.

18. The syringe as claimed in claim 17, further comprising a display region not communicating with the atmosphere.

19. The syringe as claimed in claim 16, wherein, should blood be removed by capillary effect, provision is made for the internal bore of the needle to communicate with the external atmosphere via a path providing a pressure drop such that a flow of air is allowed, while the flow of blood is limited, but that any substantial flow of the semi-solid formulation is unable to take place.

20. The syringe as claimed in claim 1, wherein the casing consists of two elements, one of which forms a hollow body into which the reservoir is introduced and the other of which contains the hollow body and traps the reservoir, said other element leaving an opening for passage of a piston rod and said one element leaving an opening for passage of the needle.

21. The syringe as claimed in claim 20, wherein the opening in said other element forms a guide for a piston rod having a diameter approximately equal to the internal diameter of the reservoir.

22. The syringe as claimed in claim 21, wherein the other element includes gripping means or finger rests.

23. The syringe as claimed in claim 1, wherein an internal diameter of the needle is between 0.2 and 1.5 mm and an internal diameter of the reservoir, and therefore the diameter of the piston of the syringe, is between 0.2 and 5 mm.

24. The syringe as claimed in claim 23, wherein a stroke of the piston has a maximum length of 7 cm in order to inject volumes of from 1 µl up to 1 ml.

25. The syringe as claimed in claim 23, wherein an external diameter of the reservoir is standardized to 6 mm, thereby allowing the aforementioned various internal diameters to be provided.

26. The syringe as claimed in claim 1, wherein, in order to avoid the risk of injection into a vessel, the syringe includes means which make it possible to check whether any blood has been withdrawn from a vessel, this being achieved without having to pull on the piston.

27. The syringe as claimed in claim 26, wherein said means is a catheter needle allowing blood to be withdrawn by the capillary effect as far as a region open to the outside.

28. The syringe as claimed in claim 1, wherein a passage for the blood from the needle passes via the reservoir and includes an elongate pressure-drop path.

29. The syringe as claimed in claim 28, wherein said elongate path is between a thread or groove on the base of the needle and a complementary surface in the transparent wall of the reservoir, or vice versa, this thread communicating at an end, directly or through a display region, with the external atmosphere via a small-diameter hole.

30. A process for filling a syringe as claimed in claim 1, wherein a filling nozzle is connected to said tube or reservoir, plugged by said piston or by a septum, and in which said piston is displaced by the filling of the formulation, said tube then being plugged by said base of the needle.

31. The filling process as claimed in claim 30, wherein said tube is packaged beforehand in a package and in which it is plugged by introducing it into the hollow body of said casing containing the needle and carrying the cap, all of this being inside a second package.

32. The syringe as claimed in claim 1, wherein a uniform conical or funnel-shaped narrowing is provided toward an end of the reservoir which houses the needle.

33. The syringe as claimed in claim 1, wherein said reservoir and said needle are assembled, at said needle base, without any bonding, clip-fastening or any other positive assembly means, ensuring assembly, and resistance to the forces tending to disassemble components of the reservoir, by means of said casing, said casing being designed to prevent axial separation of the reservoir away from the needle.

34. The syringe as claimed in claim 1, wherein the piston, which is fastened to a piston rod, has a shape which makes it possible to minimize the resistance to flow and which matches the base of the needle or that end of the reservoir on the same side as the needle so as to leave as small an unused volume as possible when the piston reaches an end-of-injection position.

35. The syringe as claimed in claim 1, forming part of a set of syringes having a constant diameter and a constant length of the reservoir tube, making it possible to use the same casing for reservoirs provided for an entire range of formulation doses.

36. The syringe as claimed in claim 1, wherein the base of the needle and the piston are made of the same material.

37. The syringe as claimed in claim 1, wherein the piston comes into direct contact with said base for the purpose of injecting the dose contained in said reservoir, so that no volume of injectable matter remains in the reservoir after the injection.

38. The syringe as claimed in claim 1, wherein the prefilling is such that the volume of the formulation occupies the entire space between the piston and the needle without it being necessary to purge the syringe before injection.

39. The syringe as claimed in claim 1, wherein the piston is not fastened to the piston rod and is pushed back by the piston rod in the injection direction.

40. The syringe as claimed in claim 1, wherein a seal is interposed between the reservoir and the casing in order to prevent any communication with an interstice located between the reservoir and the casing.

41. The syringe as claimed in claim 1, wherein said casing directly contacts said external surface of said reservoir.

42. The syringe as claimed in claim 1, wherein an entirety of said external surface of said reservoir contacts an internal surface of said reservoir.

43. A syringe configured for the parenteral injection of a semi-solid formulation, comprising:
  a hollow reservoir having a continuous longitudinal external surface, prefilled with a semi-solid preparation to be injected;
  a piston having a convex tip for pressing against the semi-solid preparation to be injected;
  a needle opening to said reservoir, said needle having a supporting base with a surface that matingly matches with said convex tip, said piston directly contacting said supporting base when said semi-solid preparation is expelled; and
  a housing surrounding an entirety of said reservoir,
  wherein an internal surface of said housing directly contacts said external surface of said reservoir along an entirety of said external surface, and
  wherein said base of said needle directly contacts an entirety of one end face of said reservoir so that said base of said needle is fixedly engaged directly between said end face of said reservoir and said housing.

* * * * *